(12) United States Patent  (10) Patent No.: US 7,484,412 B2
Hart et al.  (45) Date of Patent: Feb. 3, 2009

(54) ULTRASOUND PROBE WITH MULTIPLE FLUID CHAMBERS

(75) Inventors: Jeffrey Hart, Reedsville, PA (US); Terry Wray, McClure, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 226 days.

(21) Appl. No.: 10/599,317

(22) PCT Filed: Mar. 22, 2005

(86) PCT No.: PCT/IB2005/050986

§ 371 (c)(1),
(2), (4) Date: Sep. 25, 2006

(87) PCT Pub. No.: WO2005/096266

PCT Pub. Date: Oct. 13, 2005

(65) Prior Publication Data

US 2007/0220977 A1  Sep. 27, 2007

Related U.S. Application Data

(60) Provisional application No. 60/559,390, filed on Apr. 2, 2004.

(51) Int. Cl.
*G01N 29/04* (2006.01)
*A61B 10/00* (2006.01)
*A61B 8/00* (2006.01)

(52) U.S. Cl. .......................... 73/618; 600/437; 600/459

(58) Field of Classification Search .................. 73/661, 73/664; 367/149, 171, 172
See application file for complete search history.

(56) References Cited

U.S. PATENT DOCUMENTS

| 4,474,184 A | 10/1984 | Harui et al. |
| 4,558,706 A | 12/1985 | Nakada et al. |
| 4,807,634 A | 2/1989 | Enjoji et al. |
| 5,152,294 A | 10/1992 | Mochizuki et al. |
| 5,159,931 A | 11/1992 | Pini |
| 5,333,612 A * | 8/1994 | Wild .......................... 600/445 |
| 5,460,179 A | 10/1995 | Okunuki et al. |
| 5,531,119 A | 7/1996 | Meyers et al. |

FOREIGN PATENT DOCUMENTS

EP  0089131 A  9/1983

* cited by examiner

*Primary Examiner*—Helen C. Kwok
(74) *Attorney, Agent, or Firm*—W. Brinton Yorks, Jr.

(57) ABSTRACT

An ultrasound probe includes a transducer (46) which is mechanically oscillated to sweep beams from the transducer over an image region of a subject. The transducer is located in a first compartment of a fluid-filled chamber which is coupled to a second compartment of the fluid-filled chamber by a bubble trap tube. A drive shaft (50) which is coupled to oscillate the transducer enters and passes through the secondary chamber before terminating at the transducer oscillation mechanism in the main chamber. This locates the dynamic seal of the drive shaft which is connected between the fluid-filled chamber and the outside air so that any air leakage of the seal will leak into the secondary compartment and not into the compartment where the transducer is located.

20 Claims, 4 Drawing Sheets

ULTRASOUND PROBE WITH MULTIPLE FLUID CHAMBERS

CROSS REFERENCE TO RELATED APPLICATION

This application claims the benefit of U.S. provisional application Ser. No. 60/559,390 filed Apr. 2, 2004, which is incorporated herein.

This invention relates to medical diagnostic imaging systems and, in particular, to probes for ultrasonic imaging systems in which a transducer is mechanically swept to scan beams of ultrasound through a patient.

Mechanical ultrasound probes in which a transducer element or elements are swept to scan a patient with a series of ultrasound beams for an image are well known in the art. For example, U.S. Pat. No. 4,426,886 (Finsterwald et al.) illustrates a probe in which a motor turns a shaft which, through a bevel gear drive, oscillates an ultrasound transducer mounted on a pivot shaft. As the transducer is oscillated the direction in which the transducer facing to send and receive ultrasound is constantly changed so that the transmitted beams sweep through a plane in the patient's body. Another implementation of a mechanical probe for the same purpose is shown in U.S. Pat. No. 4,515,017 (McConaghy). In this patent a motor is connected to a rotor on which the transducer is mounted. As the motor oscillates it drives the rotor correspondingly, sweeping the beams of the transducer across the image field. When a transducer is moved inside a probe to scan a patient, it is important that there constantly exists a good coupling medium between the transducer and the acoustic window of the probe through which the ultrasound passes. Since ultrasound at imaging frequencies is highly attenuated by air and since the body has an acoustic impedance approximating that of water, the transducers of such mechanical probes are located in a fluid bath which continually provides a fluid path between the transducer and the acoustic window. In the '886 patent the fluid is water and in the '017 patent the fluid is mineral oil. To prevent problems with leaks which can develop through dynamic seals, both the transducer mechanism and the drive motor are located in the fluid chamber and surrounded by fluid. Thus, all moving components are contained within the fluid chamber and only static connections such as conductors to the motor and transducer must pass through the wall of the fluid chamber.

When the transducer being oscillated is a single element transducer or an annular array, a single beam is produced which scans an image plane of the patient. It is also known to oscillate a linear or phased array to scan a volumetric region of the patient. Such an array will statically scan a plane through electronic beam steering and when the array is moved in the elevation direction the plane will sweep through a volume, thereby enabling three dimensional imaging of the patient. U.S. Pat. No. 5,159,931 (Pini) shows a probe in which an array transducer is continually rotated about its center, thereby sweeping a plane of beams through a cylindrical volume. U.S. Pat. No. 5,152,179 (Okunuki et al.) and U.S. Pat. No. 5,152,294 (Mochizuki et al.) show probes in which a curved array transducer is oscillated back and forth to sweep a sector-shaped plane of beams through a pyramidal volume. Like the planar imaging probes, the mechanically swept transducer arrays of these probes use a fluid path to effectively conduct ultrasound between the transducer array and the acoustic window of the probe.

Fluid-filled probes are also known to develop air bubbles in the fluid. When these air bubbles travel to the region between the transducer and the acoustic window, they will interfere with the passage of ultrasound through the fluid, thereby degrading the performance of the probe. Such air bubbles can develop from changes in ambient temperature and pressure outside the fluid chamber and from tiny leaks in seals and joints of the chamber. It is also possible for a small amount of residual air to remain in the chamber and around the components inside the chamber after the chamber is filled with fluid. To address this problem, probe fluid chambers have been developed which trap air bubbles in a fluid compartment where they are kept away from the acoustic path of the transducer. U.S. Pat. No. 4,474,184 (Harui) show a probe fluid chamber with a main compartment in which the oscillating transducer is located. To the rear of the transducer is a secondary compartment joined to the main compartment by a tube extending into the secondary compartment. When held in its normal orientation with the transducer facing down toward a reclining patient, bubbles in the main compartment will float up and through the tube into the secondary compartment. As shown in the patent, the extension of the tube into the secondary compartment will prevent the bubbles from flowing back into the main compartment when the orientation of the probe changes, such as when the probe is inverted. Thus, the bubbles become trapped inside the secondary compartment from which they can be expelled the next time the fluid chamber is serviced.

In most of these mechanical probes it is seen that the motor is located inside the fluid chamber, requiring a well sealed motor and further making it difficult the service or replace the motor. In the '179 and '294 patents the motor is located outside the fluid compartment and a diaphragm seals the fluid compartment from the transducer and motor. But since the diaphragm must constantly move as the transducer array is oscillated, problems with fatigue of the diaphragm material can lead to problems with this approach. Accordingly it is desirable to provide a mechanical probe in which the motor can be located outside the fluid chamber and which reduces the possibility of bubbles interfering with the acoustic path of the transducer.

In accordance with the principles of the present invention, a mechanical ultrasound probe is provided in which the transducer is oscillated or moved to scan beams of ultrasound through an image field. The transducer is located in the main compartment of a fluid-filled chamber. A secondary chamber is located behind the main chamber and is connected to the main chamber by a bubble trap. The motive force for moving the transducer is provided by a drive shaft which extends through the secondary chamber and into the main chamber, where it connects to the transducer. The drive shaft is driven by a motor located outside of the fluid chamber. This arrangement enables the motor to be serviced or replaced easily without disturbing the fluid chamber. The drive shaft passes through primary and secondary dynamic seals in the walls of the secondary chamber. The secondary seal which connects to the ambient environment and is most susceptible to leakage would leak into the secondary chamber only where resultant bubbles are trapped, and the primary seal which connects to the main chamber is surrounded by fluid and thus immune to air leakage. In an illustrated embodiment the transducer is an electronically steered array transducer, the motion of which will sweep beams through a volumetric region of the patient.

Figure 1:
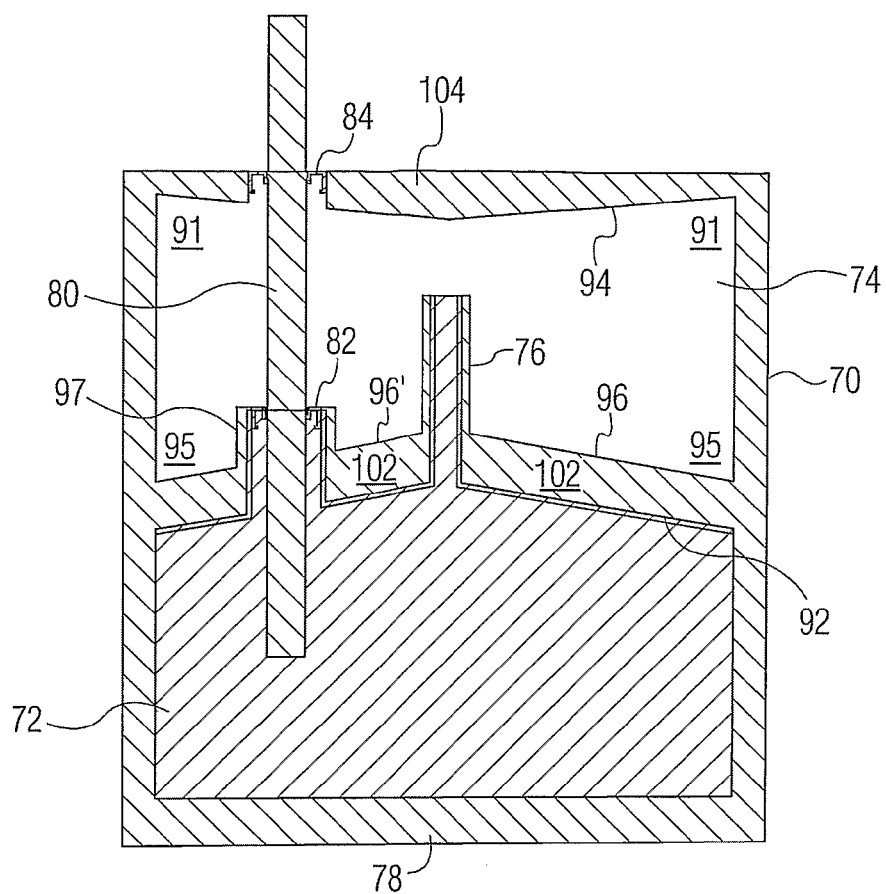
FIG. 1 is a cross-sectional view of a first embodiment of an ultrasound probe fluid chamber which illustrates the concept of the present invention.

Referring to FIG. 1, a first embodiment of a probe fluid chamber 70 of the present invention is shown in cross-section. The fluid chamber 70 has a main compartment 72 in which a moving transducer (not shown in this embodiment) is located. The transducer transmits and receives ultrasound through an acoustic window located at the end 78 of the main compartment. The transducer is moved in its scanning motion by a drive force provided by a drive shaft 80 which is oscillated or rotated by motor located outside of the fluid chamber. Behind the main compartment 72 is a secondary compartment 74. The main compartment is connected to the secondary compartment by a bubble trap tube 76. The purpose of the secondary compartment is to trap any bubbles that develop in the main compartment 72 around the transducer, and which could flow between the transducer and the acoustic window and thus interfere with the transmission and reception of ultrasound through the fluid in front of the transducer. This is accomplished by providing the bubble trap tube 76 to conduct bubbles to the secondary compartment. Since the bubble trap tube is relatively small and extends into the secondary compartment beyond the wall 102 that divides the two compartments, bubbles will tend to remain in the secondary compartment and be unlikely to float back into the main compartment even when the probe and its fluid chamber is inverted. When the probe is in its usual operating orientation with the secondary compartment above the main compartment as shown in FIG. 1, bubbles floating up into the secondary compartment will remain against the upper wall 94 of the secondary compartment. When the probe is inverted the bubbles will float up to the opposite wall 96 of the secondary compartment, with the likely exception of a bubble located immediately above the bubble trap tube 76 at the time of and during the inversion of the probe.

The embodiment of FIG. 1 includes further measures to rapidly conduct bubbles in the main compartment to the secondary compartment and keep them trapped there. It can be seen that the upper surface 92 of the main compartment is sloped upward toward the center of the compartment where the bubble trap tube is located. Thus, bubbles developing in the main compartment 72 will tend to float to the upper surface 92 of the compartment, then upward along the upper surface until reaching and floating up through the bubble trap tube. The upper surface 94 of the secondary compartment is seen to slope upward from the center of the compartment above the bubble trap tube to the periphery of the compartment. Thus, bubbles floating up through the bubble trap tube and to the upper surface 94 of the secondary compartment will then continue to travel upward along the upper surface 94 until reaching the outer periphery 91 of the compartment 74. The bubbles will then tend to stay at the corners 91 of the secondary compartment, the highest point to which they can travel. If the probe is then inverted, the bubbles will tend to float up and to the periphery 95 of the surface 96 of the secondary compartment, which is the upper surface of the secondary compartment when the probe is inverted from the orientation shown in FIG. 1. It is seen that this surface 96 is also sloped upward from the center to the periphery of the compartment when the probe is in the inverted position, further aiding to conduct bubbles to the periphery 95 of the compartment 74. This sloping of the internal walls of the compartments conducts bubbles to locations in the secondary compartment 74 from which they are unlikely to be able to travel back to the main compartment 72.

The drive shaft 80 which supplies the motive force to oscillate or rotate the transducer is seen to enter the main compartment 72 by first passing through the secondary compartment 74. Since the drive shaft 80 is a moving component it must pass through dynamic seals 82, 84 in the walls through which it passes that allow this motion. The secondary seal 84 which seals the drive shaft interface between the outside of the chamber and the interior of the secondary compartment 74 has air on one side (the outside) of the seal and fluid on the other side of the seal (inside the chamber). The primary seal 82 at the passage of the drive shaft from the secondary to the main compartment has fluid on both sides of the seal. Thus, if both seals were to begin to leak, the secondary seal 84 is much more likely to pass air into the chamber 70 than is the primary seal. Since air leakage through the secondary seal 84 will only leak air into the secondary compartment 74, the bubbles from such a leak will be contained and trapped in the secondary compartment and be unlikely to enter the main compartment. Thus, the passage of the drive shaft through the secondary compartment reduces the likelihood that a leaking shaft seal will admit bubbles into the main compartment where the transducer is located.

Furthermore, in this embodiment it is seen that the primary seal 82 is not simply located in the wall 102 between the compartments, but is located in a cylindrical upward projection 97 from that wall. Any bubbles trapped in the corners 91 of the secondary compartment will naturally float upward to the corners 95 of the secondary compartment when the probe is inverted, and any bubble not yet in corners 91 at the time of inversion that float to the surface 96' will travel around the projection 97 and not into the seal 82 as the bubble travels upward and outward to the corners 95 of the inverted probe.

Figure 2:
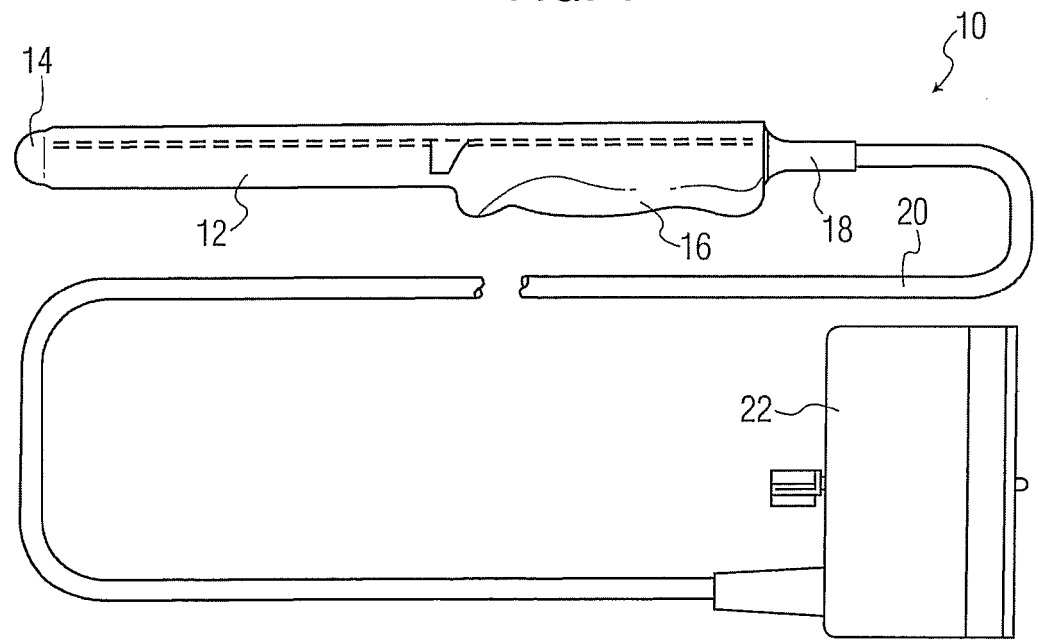
FIG. 2 illustrates a typical intracavity ultrasound probe of the prior art.

In a constructed embodiment, a dual chamber bubble trap in accordance with the present invention is used in an intracavity ultrasound probe which scans a volumetric region inside the body. Referring now to FIG. 2, a typical intracavity ultrasound probe 10 of the prior art is shown. This probe includes a shaft portion 12 of about 6.6 inches (16.7 cm) in length and one inch (2.54 cm) in diameter which is inserted into a body cavity during use. The ultrasound transducer is located in the distal tip 14 of the shaft. In this probe the transducer is a static curved array transducer which is able to scan a planar sector around the tip of the probe. The probe is grasped and manipulated by a handle 16 during use. At the end of the handle is a strain relief 18 for a cable 20 which extends about 3-7 feet and terminates at a connector 22 which couples the probe to an ultrasound system. A typical two dimensional imaging IVT probe such as the one shown in FIG. 1 may have a shaft and handle which is 12 inches in length and weigh about 48 ounces (150 grams) including the cable 20 and the connector 22.

Figure 3:
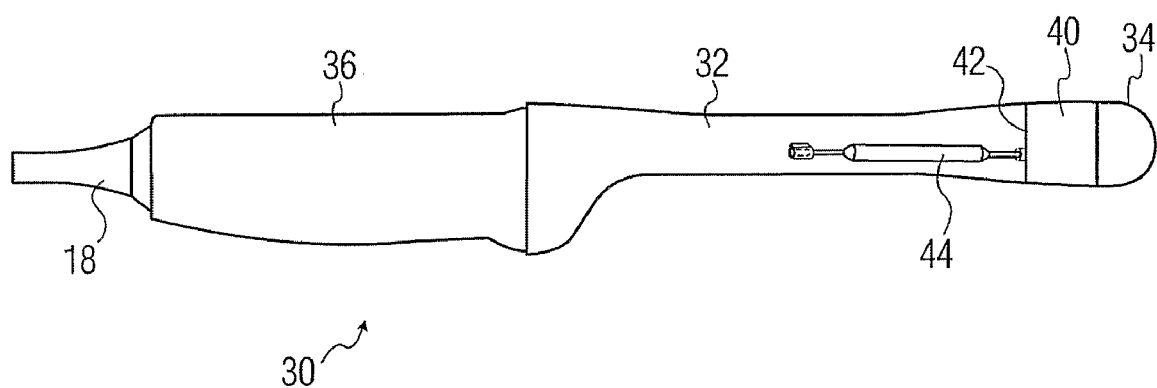
FIG. 3 illustrates a partially cut-away side view of an intracavity probe for three dimensional imaging which is constructed in accordance with the principles of the present invention.
Figure 4:
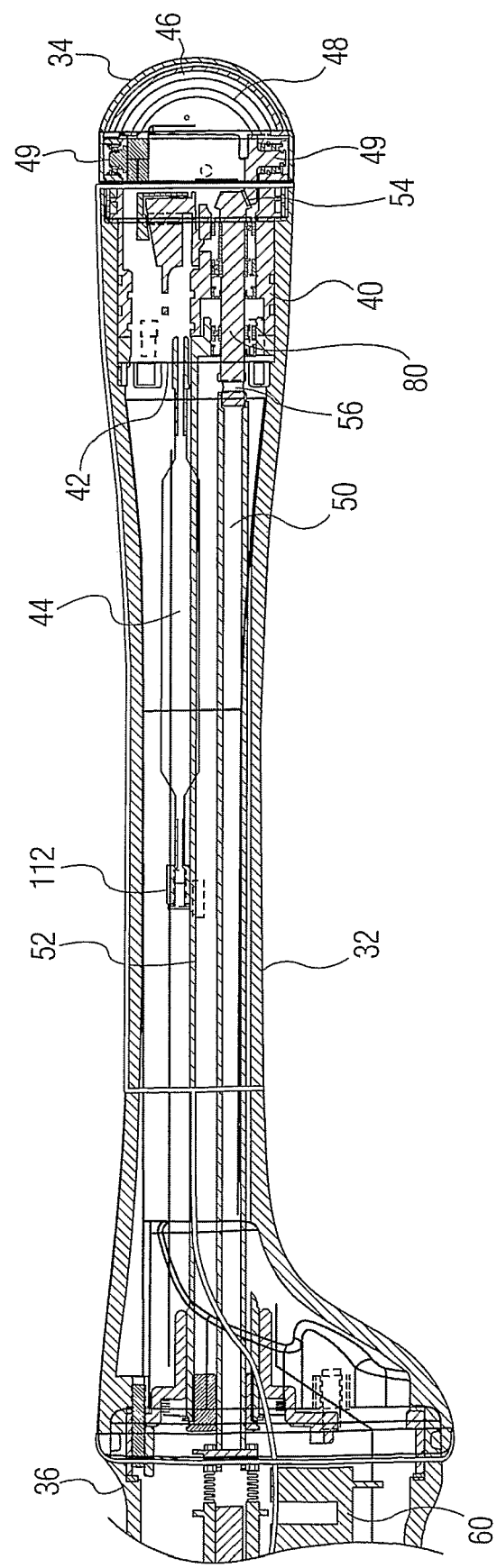
FIG. 4 is a side cross-sectional view of a 3D intracavity probe constructed in accordance with the principles of the present invention.

Referring now to FIG. 3, an intracavity ultrasound probe 30 for three dimensional imaging which is constructed in accordance with the principles of the present invention is shown. The probe 30 includes a handle section 36 by which the user holds the probe for manipulation during use. At the rear of the handle is a strain relief 18 for the probe cable (not shown). Extending from the forward end of the handle 36 is the shaft 32 of the probe which terminates in a dome-shaped acoustic window 34 at the distal end through which ultrasound is transmitted and received during imaging. Contained within the distal end of the shaft is a transducer mount assembly 40 which is also shown in the uncovered views of the tip assembly of FIGS. 4 and 5. A convex curved array transducer 46 is attached to a transducer cradle 48 at the distal end of the assembly 40. The transducer cradle 48 is pivotally mounted by its pivot axis 49 to be rocked back and forth in the distal end of the probe and thereby sweep an image plane through a volumetric region in front of the probe. The transducer cradle 48 is rocked by an oscillating drive shaft 50 which extends from a motor and position sensor 60 in the handle 36 to the transducer mount assembly 40. The drive shaft 50 extends through an isolation tube 52 in the shaft which serves to isolate the moving drive shaft from the electrical conductors and volume compensation balloon 44 located in the shaft proximal the transducer mount assembly 40. The drive shaft 50 is connected by a coupling 56 to a pinion shaft 80 of the transducer mount assembly 40. The pinion shaft 80 rocks the cradle 48 by means of two mating bevel gears 54, one at the end of the pinion shaft 80 and another on the transducer cradle 48. The motor alternately drives the drive shaft 50 and the pinion shaft 80 in one direction of rotation and then the other, which alternately rocks the transducer cradle 48 in one direction and then the other, which sweeps the image plane of the transducer array 46 back and forth through the volumetric region in front of the distal end of the probe. The echo signals acquired by the transducer array 46 are beamformed, detected, and rendered by the ultrasound system to form a three dimensional image of the volumetric region scanned by the probe.

Figure 5:
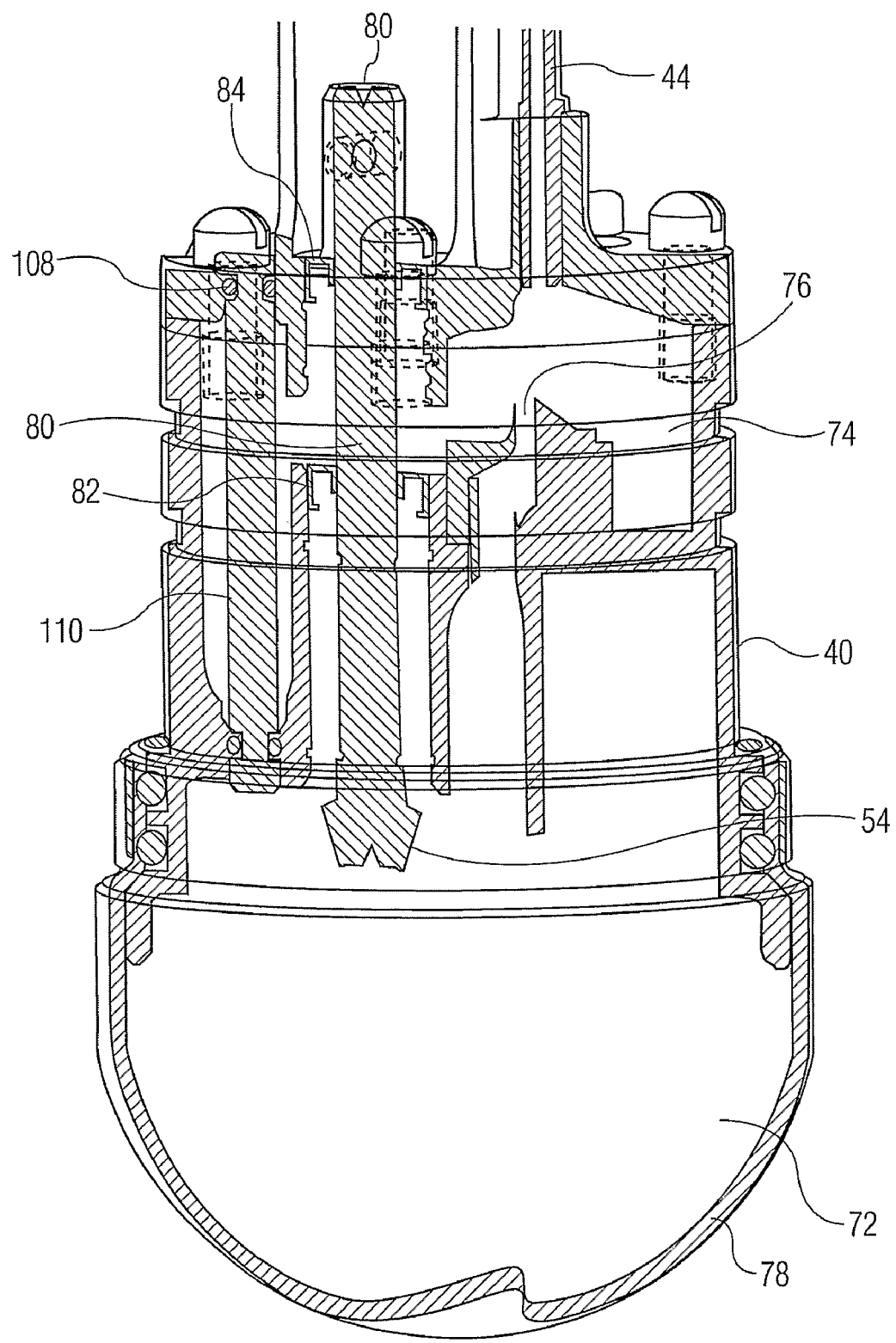
FIG. 5 is a partially cross-sectional and perspective view of the fluid chamber of a 3D intracavity probe constructed in accordance with the principles of the present invention.

Because ultrasonic energy does not efficiently pass through air, the array transducer 46 is surrounded by a liquid which is transmissive of ultrasound and closely matches the acoustic impedance of the body which is approximately that of water. The liquid is contained within a fluid chamber 42 inside the transducer mount assembly 40 which also contains the array transducer 46. Water-based, oil-based, and synthetic polymeric liquids may be used. In a constructed embodiment silicone oil is used as the acoustic coupling fluid in the transducer fluid chamber. Referring to FIG. 5, a partial cross-sectional and cutaway view of the transducer mount assembly 40 is shown. The fluid chamber 42 of the assembly 40 has a main compartment 72 in which the transducer cradle 48 and array transducer 46 (see FIG. 4) are located. The pinion shaft 80 is seen extending into the main compartment 72, terminating in a bevel gear 54. The pinion shaft 80 is seen to be supported by primary and secondary seals 82 and 84. The main compartment 72 is connected to an upper compartment 74 of the fluid chamber by a bubble trap tube 76. The secondary seal 84 seals the pinion shaft as it passes from outside the fluid chamber into the secondary compartment of the chamber. The primary seal 82 seals the pinion shaft 80 as it passes from the secondary compartment to the main compartment of the fluid chamber. Located at the top of the upper compartment 74 in this embodiment is the fill port 108 for the fluid chamber which is sealed by a fill pin 110. Connected to the assembly 40 above the bubble trap tube 76 in this embodiment is the volume compensation balloon 44 for the fluid chamber which is sealed at its proximal end by a threaded plug 112 (see FIG. 4). As fluid is injected into the fluid chamber through the fill port 108 it drops directly into the main compartment 72, filling the main compartment first. The secondary compartment 74 fills next and finally the volume compensation balloon fills. When the fluid chamber and balloon are full the fill port is sealed with the fill pin 110 and the threaded plug 112 at the end of the volume compensation balloon seals the proximal end of the balloon as described in concurrently filed U.S. patent application Ser. No. 60/559,379, entitled ULTRASONIC PROBE VOLUME COMPENSATION SYSTEM, the contents of which are incorporated herein by reference. Any bubbles remaining or developing in the main fluid compartment 72 will tend to float up through the bubble trap tube 76 to the secondary compartment 74, (and possibly then into the balloon 44 in the embodiment of FIGS. 3-5) where they will remain until expelled later. Of the two seals for pinion shaft 80, it is the secondary seal 84 between the fluid chamber and the exterior environment which would leak air rather than the primary seal 82 between the two compartments. Thus, bubbles resulting from air leakage around the shaft 80 will be entering the secondary compartment 74 where they will remain trapped and be unlikely to make their way into the main compartment where the transducer array 46 is located.

Other embodiments and variations of the present invention will readily occur to those skilled in the art. For example, rather than being rocked the array transducer could be spun about its center axis by a rotating shaft extending into the main chamber. A spinning array transducer could sweep beams through a cylindrical volume or conical volume rather than the wedge-shaped volume swept by a rocking array transducer. The bubble trap tube could be located at one side of the two compartments, with a surface in the main compartment promoting the travel of bubbles to the side of the chamber where the bubble tube is located and a surface in the secondary compartment promoting the travel of bubbles to the other side of the chamber away from the tube.

What is claimed is:

1. An ultrasound probe which scans a subject with beams of ultrasound transmitted by a moving transducer comprising:
   a fluid-filled chamber having a main compartment in which the transducer is movably mounted;
   a secondary compartment of the fluid-filled chamber having an interior surface which conducts bubbles away from a fluid-filled passageway connecting the main and secondary compartments when the probe is held in a given orientation,
   wherein the passageway connecting the main and secondary compartments is accessed at a point in the main compartment to which bubbles are designed to flow when the probe is held in the given orientation; and
   a drive mechanism extending into the fluid-filled chamber which supplies a motive force for the transducer, the drive mechanism passing through a drive mechanism passageway connecting the main and secondary compartments and terminating in the main compartment of the fluid-filled chamber.

2. The ultrasound probe of claim 1, wherein the drive mechanism further comprises a drive shaft.

3. The ultrasound probe of claim 2, further comprising a motor, located outside the fluid-filled chamber and coupled to the drive shaft for oscillating or rotating the drive shaft.

4. The ultrasound probe of claim 2, further comprising a secondary seal by which the drive shaft passes from outside the fluid-filled chamber into the secondary compartment, and a primary seal by which the drive shaft passes from the secondary compartment to the main compartment.

5. The ultrasound probe of claim 4, wherein the seals comprise dynamic seals permitting drive shaft motion.

6. The ultrasound probe of claim 5, further comprising fluid located on both sides of the primary seal and fluid located on only one side of the secondary seal,
   wherein leakage of the secondary seal may admit air into the secondary compartment.

7. The ultrasound probe of claim 1, wherein the fluid-filled passageway further comprises a bubble trap tube.

8. The ultrasound probe of claim 7, wherein the bubble trap tube further comprises a tube extending from a wall dividing the main and secondary compartments into the secondary compartment.

9. The ultrasound probe of claim 1, wherein the transducer comprises an array transducer which may be controlled to electronically steer beams over a planar region,
   wherein motion of the array transducer causes the beams to be swept over a volumetric region.

10. The ultrasound probe of claim 9, wherein the transducer is movably mounted on a pivoting mechanism which permits the array transducer to be oscillated back and forth in an elevation direction,
    wherein oscillation of the pivoting mechanism is motivated by the drive mechanism.

11. The ultrasound probe of claim 10, wherein the drive mechanism further comprises a drive shaft connected to the pivoting mechanism by a gear mechanism.

12. The ultrasound probe of claim 9, wherein the fluid-filled chamber is enclosed by an acoustic window through which ultrasound beams are transmitted as the array transducer is moved.

13. The ultrasound probe of claim 12, further comprising a fluid-filled space located between the transmitting surface of the array transducer and the acoustic window as the array transducer is moved.

14. An ultrasound probe which scans a subject with beams of ultrasound transmitted by a moving transducer comprising:
    a fluid-filled chamber having a main compartment in which the transducer is movably mounted;
    a secondary compartment of the fluid-filled chamber;
    a wall separating the main and secondary compartments which is sloped to an uppermost location;
    a fluid-filled passageway located at an uppermost location in the main compartment and connecting the main and secondary compartments; and
    a drive mechanism extending through a drive mechanism passageway of the wall and terminating in the main compartment which supplies a motive force for the transducer,
    wherein the main compartment exhibits an interior surface which promotes the travel of bubbles in the main compartment toward the fluid-filled passageway when the probe is held in a given orientation, and wherein the secondary compartment exhibits an interior surface which promotes the travel of bubbles in the secondary compartment away from the fluid-filled passageway when the probe is held in the given orientation.

15. The ultrasound probe of claim 14, wherein the fluid-filled passageway is located at or near the center of the fluid-filled chamber.

16. The ultrasound probe of claim 14, wherein the fluid-filled passageway further comprises a bubble trap tube.

17. The ultrasound probe of claim 14, wherein the transducer comprises an array transducer which may be controlled to electronically steer beams over a planar region,
    wherein motion of the array transducer causes the beams to be swept over a volumetric region.

18. The ultrasound probe of claim 14, wherein the drive mechanism is coupled to a motor located outside the fluid-filled chamber.

19. The ultrasound probe of claim 18, wherein the drive mechanism comprises a drive shaft.

20. The ultrasound probe of claim 19, wherein the drive mechanism further comprises a gear mechanism.

* * * * *